United States Patent
Wess et al.

(10) Patent No.: US 12,048,447 B2
(45) Date of Patent: Jul. 30, 2024

(54) DIFFUSER FOR A SHOCKWAVE TRANSDUCER

(71) Applicant: Storz Medical AG, Tägerwilen (CH)

(72) Inventors: Othmar Wess, Lengwil-Oberhofen (CH); Jürgen Mayer, Reichenau (DE)

(73) Assignee: STORZ MEDICAL AG, Tägerwilen (CH)

( * ) Notice: Subject to any disclaimer, the term of this patent is extended or adjusted under 35 U.S.C. 154(b) by 0 days.

(21) Appl. No.: 18/239,870

(22) Filed: Aug. 30, 2023

(65) Prior Publication Data

US 2024/0122616 A1    Apr. 18, 2024

Related U.S. Application Data

(63) Continuation of application No. PCT/EP2022/055356, filed on Mar. 3, 2022.

(51) Int. Cl.
*A61B 17/225* (2006.01)
*A61B 17/22* (2006.01)

(52) U.S. Cl.
CPC .... *A61B 17/2251* (2013.01); *A61B 17/22004* (2013.01); *A61B 2017/2253* (2013.01)

(58) Field of Classification Search
CPC .......... A61B 17/2251; A61B 17/22004; A61B 2017/2253
See application file for complete search history.

(56) References Cited

U.S. PATENT DOCUMENTS

| | | | |
|---|---|---|---|
| 4,721,108 A | | 1/1988 | Heine et al. |
| 5,033,456 A | * | 7/1991 | Pell ........ G10K 15/043 601/4 |
| 5,048,527 A | * | 9/1991 | Okazaki ........ A61B 17/2251 601/4 |
| 5,174,280 A | * | 12/1992 | Gruenwald ........ G10K 15/043 367/175 |
| 5,309,897 A | * | 5/1994 | Hassler ........ G10K 15/043 601/4 |
| 5,810,748 A | * | 9/1998 | Ueberle ........ A61B 17/2251 601/4 |

(Continued)

FOREIGN PATENT DOCUMENTS

| | | |
|---|---|---|
| JP | H02274242 A | 11/1990 |
| JP | H0377549 A | 4/1991 |

(Continued)

OTHER PUBLICATIONS

PCT International Search Report and Written Opinion, PCT/EP2022/055356, Jun. 22, 2022, 13 pages.

(Continued)

*Primary Examiner* — Julian W Woo
(74) *Attorney, Agent, or Firm* — Quarles & Brady LLP; Yakov S. Sidorin

(57) ABSTRACT

A shockwave transducer for a lithotripter includes a shockwave source and a body with an exit aperture. The transducer is configured to generate a shockwave propagating from the body and through the exit aperture. The body comprises at least one diffuser, which engages into the shockwave propagating from the body. This diffuser includes a material characterized by a propagation velocity of the shockwave that is different from the propagation velocity of the shockwave in the surrounding medium.

15 Claims, 8 Drawing Sheets

(56) References Cited

U.S. PATENT DOCUMENTS

| | | | | |
|---|---|---|---|---|
| 5,897,495 | A | * | 4/1999 | Aida ................... A61N 7/022 |
| | | | | 601/4 |
| 7,559,904 | B2 | * | 7/2009 | Ein-Gal ............. A61B 17/2258 |
| | | | | 601/4 |
| 2010/0137754 | A1 | | 6/2010 | Zhou |

FOREIGN PATENT DOCUMENTS

| | | |
|---|---|---|
| JP | H04263848 A | 9/1992 |
| JP | H05123330 A | 5/1993 |
| JP | H06230489 A | 8/1994 |
| WO | 0166189 A1 | 9/2001 |
| WO | 2013182800 A2 | 12/2013 |

OTHER PUBLICATIONS

Japan Patent Office, Notice of Reasons for Refusal, Application No. 2023-553429, Feb. 7, 2024, 14 pages.

\* cited by examiner

DIFFUSER FOR A SHOCKWAVE TRANSDUCER

CROSS-REFERENCE TO RELATED APPLICATIONS

This application is a continuation of pending International Application No. PCT/EP2022/055356 filed on Mar. 3, 2022 and now published as WO 2022/184810, which designates the United States and claims priority from European Application No. 21160785.8 filed on Mar. 4, 2021. The disclosure of each of the above-identified patents is incorporated herein by reference in their entirety for all purposes.

FIELD OF THE INVENTION

The invention relates to a device for reducing the number and/or size of cavitation cavities generated by a shockwave transducer of a medical shockwave device, such as a lithotripter, without compromising the effectiveness of the shockwaves.

DESCRIPTION OF RELATED ART

In WO 01/66189 A1 high intensity focused ultrasound heating is provided by applying therapeutic ultrasonic waves using an array of transducers. Cavitation is detected by using some or all of the transducers in the array to detect ultrasonic waves emanating from or reflected from the patient's body or the interface. A feedback signal is generated based on such detection. If the feedback signal indicates the presence of cavitation, the therapeutic ultrasonic waves are terminated or altered.

SUMMARY OF THE INVENTION

Shockwave transducers in medical shockwave devices such as lithotripters generate shockwaves in a medium, e.g. water, and couple them into a human or animal body. The shockwaves travel through the medium in which they were generated and into the body to the target area. The shockwaves are focused to a target area in the body. The target area can be a concretion inside the body e.g. a kidney stone or specific soft tissue areas.

Normally, a positive pressure pulse of the shockwave is followed by a smaller negative pressure pulse (tensile wave). Cavitation cavities, also called cavitation bubbles or cavitation voids, are created by the negative pressure wave associated with the shockwave. Negative pressure waves are generated especially at the edge of the aperture by a diffraction wave. Although they usually propagate divergently, i.e. with decreasing amplitude, there exist spatial regions in which they concentrate and generate considerable negative pressure by phase-locked superposition. In these superposition zones mostly on the axis of the shockwave source and the surrounding area. Cavitation cavities collapse within microseconds, generating local spherical shockwaves, which are responsible for undesirable damage to biological tissue. In particular, they can cause injury (usually in the form of petechial hemorrhages and hematomas) when in contact with tissue (blood vessels, capillaries).

The problem to be solved by the invention is to reduce damage of body tissue and to reduce injuries, such as hematoma, while reducing the size of concretions or treatment of soft tissue. Another object of the invention is to reduce the generated cavitation cavities, without compromising the effectiveness of the shockwaves. A further object of the invention is to avoid a deactivation of the device or an interruption or termination of the treatment when cavitation takes place.

Solutions of the problem are described in the independent claims. The dependent claims relate to further improvements of the invention.

In an embodiment, a shockwave transducer may include a shockwave source and a body having an exit aperture. The body may have a void filled with a shockwave conducting medium. The body may hold the shockwave source. The shockwave source may be configured to generate shockwaves. Typically, a shockwave may be a type of propagating disturbance in a medium, e.g. fluid (e.g. water), gas or plasma. A shockwave may carry energy, can propagate through a medium, and may be characterized by an abrupt, nearly discontinuous, change in pressure, temperature, and density of the medium.

The body further includes an exit aperture for the shockwaves to exit the body. The transducer may be configured to direct the shockwaves propagating through the exit aperture.

The body may further include at least one reflector and/or focusing element. A reflector may have an elliptic or parabolic shape. A lens may be provided for focusing. In an embodiment, the reflector may be a sphere segment holding piezo electric devices. Shockwaves generated by the shockwave source may exit the body through the exit aperture.

The geometry of the body depends on the shockwave source. The shockwave source may be a point source, a planar source or a cylindrical source. A point source may include an ellipsoidal reflector, a planar source an acoustic lens and a cylindrical source a parabolic reflector. The shockwave transducer may include a cylindrical source with a parabolic reflector.

The body may have a top face, a bottom face, an inner surface, an outer surface, a rim, a center axis and an exit aperture. The rim may enclose the exit aperture. The void of the body may be the three-dimensional space defined by the inner surface of the body and a plane passing through the rim.

The shockwave source may include a coil. The coil may have a cylindrical shape. The coil may be located at the center axis of the reflector. Alternatively, the shockwave source may include a flat coil or a piezo element or a spark gap.

The shockwave source may be configured to generate a shockwave propagating from the transducer. The shockwave transducer may be connected to a power generator. The power generator may generate a high power signal. This high power signal may be applied to the shockwave source, generating a shockwave. The shockwave propagates from the transducer and may be guided, reflected or directed to a focus area.

The shockwave transducer may include a shockwave source with a cylindrical coil. The coil may be arranged within a body, the body further including a reflector. The cylindrical coil may be arranged with its center axis at a reflector center axis. The cylindrical coil may generate a cylindrical wave propagating in a radial direction of the coil and may be symmetrical to the center axis. This wave may be reflected by the reflector towards a focus area, which also may be a focus point. The focus area may be on the center axis and distant from the coil. The distance may be in a range between 2 cm and 25 cm depending on the design of the reflector and the coil to leave sufficient space for positioning a patient such that a concretion can be disintegrated or a soft tissue target area can be treated. The entirety of the waves propagating from the shockwave source to the focus area or focus point, define a wave propagation area.

This wave propagation area may be located inside a volume defined by the void of the body. It may further extend beyond the body in a volume, which can be approximated in a region close to the rim by a cylindrical space. The cylindrical space may have the same base as the exit aperture. The cylindrical space may have the same inner diameter as the rim of the body. The cylindrical space may extend from the body. The cylindrical space may extend from the body and coaxial to the center axis of the body. The cylindrical space may extend up to 0.5 cm, 1 cm, 2 cm, 5 cm, 10 cm, 30 cm or 50 cm from the rim of the body. The cylindrical space may have a volume. The volume may be a three-dimensional space enclosed by a physical, preferably an imaginary extension of the rim along the direction of the propagating wave and enclosing the wave propagation area. The body and the cylindrical space may have a joint volume. The joint volume may be the volume of the void of the body combined with the volume of the cylindrical space. In other words, the joint volume may be the three dimensional space defined the inner surface of the body and three-dimensional space enclosed by the cylindrical space.

The shockwave transducer may include at least one diffuser. The body of the shockwave transducer may include the at least one diffuser. The least one diffuser may engage into the shockwave propagating from the shockwave source. The at least one diffuser may engage into the wave propagating from the body and through the exit aperture. From a geometrical perspective, the at least one diffuser may extend into a volume defined by the body, and/or a cylindrical space where the cylindrical space has the same inner diameter as the rim of the of the body, which may be the exit aperture.

The body has a void filled with a shockwave conducting medium and the at least one diffuser includes a material with a propagation velocity of the shockwave different from that in the conducting medium and/or the at least one diffuser includes a shockwave reflecting material. The shockwave conducting medium may be water.

The body may include at least one diffuser arranged at the exit aperture and the at least one diffuser includes a material with a different propagation velocity than the propagation velocity of the shockwave in the conducting medium and/or the at least one diffuser includes a shockwave reflecting material. The at least one diffuser may be rigidly arranged at the exit aperture, wherein rigidly means that the diffuser may not pivot, swivel or turn. This has the advantage that the diffuser stays does not move or dislocate, when a force is applied to the diffuser. Additionally a rigid diffuser makes the handling of the transducer and the medical shockwave device safer and more convenient. Further, the diffuser cannot be misaligned.

The different propagation velocity and/or reflection of the material generate phase shifts and counteracts the constructive interference which leads to cavitation cavities and ultimately causes damage to the body tissue. The material of the at least one diffuser can be adapted according to the shockwaves generated by the shockwave source. Depending on the adapted material chosen, the shockwaves can be refracted, reflected, diffracted, transmitted and/or absorbed. The material of the at least one diffuser may include a material having a propagation speed differing from the propagation speed of water.

The material, may include a material having a low absorption. The absorption may be less than 50%. An absorbing material may cause attenuation of the shockwaves, compromising the effectiveness of the shockwaves and ultimately of the lithotripter The at least one diffuser may be located at the body and/or be the body itself. The at least one diffuser may include at least one segment. If the at least one diffuser includes more than one segment, these segments may be coupled to the body separately. The at least one diffuser may be monolithic and include only one piece. The at least one diffuser may be annular, but any outer form known to the person skilled in the art is also possible.

The at least one diffuser may be located on the inner surface of the body, coupled to the top face of the body, be formed by the body, located at the rim of the body, preferably the at least one diffuser may be located on the rim of the body. The at least one diffuser may also be located on the inner surface of the body and below the rim of the body. Locating the diffuser on or at the rim of the body has the advantage, that the device can be placed directly on the treated individual's body. This may be particularly advantageous when treating obese individuals who occupy the entire space between the rim and the focus area or focus point located in the patient. By locating the at least one diffuser on or at the rim of the body, the treatment depth may be not shortened and the device can be reliably applied for the treatment of individuals of every size.

The at least one diffuser may be an outer diffuser being arranged annular at an outer circumference of the exit aperture and/or the at least one diffuser may be an inner diffuser being arranged annular at an inner circumference of the exit aperture.

The at least one diffuser may include grooves and/or protrusions distributed around its circumference.

The grooves and/or protrusions may be distributed irregularly around the circumference of the outer diffuser and/or inner diffuser.

The material of the at least one diffuser may be metallic material, a nonmetallic inorganic material or preferably a polymeric material (e.g. polyethylene,polystyrene). The different propagation velocity and/or the reflection of the at least one diffuser may alter the phase and/or amplitude of the wave, by causing refraction and diffraction. The material of the at least one diffuser may not absorb the wave. Since an absorption may cause attenuation of the wave, compromising the effectiveness of the shockwave transducer.

The diffuser has the effect, that the shockwave is altered locally in its phase and/or amplitude and/or the shockwave is reflected. The reflection may be specular and/or non-specular. The diffuser may have the effect that the shockwaves are scattered into non-specular directions and thereby cause a diffuse reflection. The outer diffuser and/or inner diffuser may counteract a constructive interference of the shockwaves in superposition zones. Consequently, only a diffuse superposition with significantly reduced peak values can occur.

The at least one diffuser, which may be an inner and/or outer diffuser, may have a top side, a bottom side, a transducer-facing side and a transducer-averted side. The transducer-facing side may be the part of the diffusers interacting with the waves. The top side may be the part facing away from the body, the bottom side may be the part of the diffuser facing the body. The transducer-averted side of the outer diffuser may be the part of the outer diffuser, facing away from the transducer. The transducer-averted side of the inner diffuser may be the part of the diffuser facing the center axis of the shockwave source. The transducer-averted side may have no grooves and protrusions.

The groves and/or protrusions of the respective diffusers may be located at the transducer-facing side of the diffusers. The outer diffuser may be coupled to the body on the bottom side of the outer diffuser. The inner diffuser may be coupled to the shockwave source on the bottom side of the inner diffuser. In other words, the outer and/or inner diffuser may be coupled to the transducer on their bottom side. The inner and/or outer diffuser may be coupled to the transducer by a detachable connection, a fixed connection and/or may be integrated into the body. The inner and/or outer diffuser may be rigidly coupled to the transducer. The inner and/or outer diffuser may not pivot, swivel and/or turn. A rigid detachment prevents the displacement of the inner and/or outer diffuser, when a force is applied to the diffuser. A detachable connection may be accomplished by a positive fit and/or a frictional connection, such as a clamp, a bayonet coupling, a thread, a plug connection or any other detachable connection known to the person skilled in the art is also possible. A fixed connection may be accomplished by an adhesive bond, such as gluing or welding. The body and the at least one diffuser may also be integral and/or monolithic.

Alternatively, the at least one diffuser may be integrated into the body. In other words the body itself may be the at least one diffuser or part thereof. For example, the body may be the outer diffuser. The grooves of the at least one diffuser may be formed by recesses and/or notches within the body. The grooves may penetrate the rim and/or the inner surface of the body, but may not penetrate through the outer surface of the body. The protrusions of the at least on diffuser may be the part of the body without the grooves. In other words, the protrusions may be the part of the body without recesses in the rim and/or the inner surface. Therefore, the diffuser includes a shockwave reflecting material from the body. This may be metal, e.g. steel, brass, tin or aluminum. The grooves may be inserted into the body e.g. by cutting, milling, drilling and/or sawing. The grooves inserted into the body be approximately rectangular, triangular and/or parabolic.

The outer diffuser may also be the body itself with a complementary diffuser coupled to the rim. The transducer facing side of the complementary diffuser may face the grooves of the diffuser integrated into the body.

Since the inner and/or outer diffuser can be coupled to the shockwave transducer, almost every shockwave transducer and/or medical shockwave device, e.g. lithotripter, can be retrofitted with an inner and/or outer diffuser. Therefore, it is possible to decrease the possibility of injuries in a cheap and convenient way.

The grooves and protrusions of the inner diffuser or the outer diffuser or the inner and the outer diffuser, may be distributed irregularly around the circumference of the inner diffuser and/or the outer diffuser.

A regular distribution causes a homogeneous wave to be protruded from the body, causing a homogeneous pressure distribution. The advantage of an irregular distribution is that constructive interference and resonance can be avoided. Since constructive interference and resonance is the source of cavitation cavities, the effects of cavitation cavities can be minimized by an irregular distribution of the grooves and/or protrusions around the circumference of the inner and/or outer diffuser. Consequently, damage of body tissue and injuries are reduced.

The protrusions may protrude radially with respect to the center axis of the body. The protrusions of the outer diffuser may protrude towards the center axis and the protrusions of the inner diffuser may protrude away from the center axis.

The protrusion of the outer diffuser or the protrusion of the inner diffuser may protrude into the area defined by the wave propagating out of the reflector. Alternatively, the protrusion of the inner diffuser and the outer diffuser may protrude into the area defined by the wave propagating out of the reflector.

This area defined by the wave propagating out of the body and through the exit aperture may be located inside a joint volume defined by the body and a cylindrical space. The cylindrical space may have the same inner diameter as the rim of the body. The cylindrical space may have the same base as the exit aperture. The cylindrical space may extend from the body. The cylindrical space may extend up to 0.5 cm, 1 cm, 2 cm, 5 cm, 10 cm, 30 cm or 50 cm from the rim of the body. The cylindrical space may define a volume. Therefore, the protrusions of the inner diffuser or the outer diffuser or both of the inner and the outer diffuser may protrude into the joint volume defined by the body and the volume defined by the cylindrical space. Hence, the inner diffuser and/or the outer diffuser may engage into the wave propagating from the body.

The depth of the grooves of the outer and/or inner diffuser may be adapted to the generated shockwaves. The depth of the groove may be in a range between 1 mm and 40 mm, preferably 1 mm-10 mm.

The outer diffuser and/or the inner diffuser may have a thickness of 1 mm-40 mm. Thickness of the outer diffuser and/or the inner diffuser may vary from the transducer-averted side to the transducer-facing side of the outer and/or the inner diffuser. The Thickness of the outer and/or inner diffuser may be reduced from the transducer-averted side to the transducer-facing side. Consequently, the outer and/or inner diffuser may be conic or tapered. A conic or tapered form of the diffuser also aids to counteract the constructive interference of the shockwaves.

In an embodiment, the body may be a reflector. A reflector may be any means capable of reflecting the shockwaves generated by a shockwave source. The reflector may be a concave reflector. The reflector may have a top face, a bottom face, an inner surface, an outer surface, a rim and a center axis. The reflector may be rotationally symmetric. The reflector may define a void. The void may have a volume. The volume of the reflector may be the three-dimensional space defined by the inner surface of the reflector and a plane passing through the rim.

The shockwave transducer may include a shockwave source with a cylindrical coil. The cylindrical coil may be arranged with its center axis at the reflector center axis. The cylindrical coil may generate a cylindrical wave propagating in a radial direction of the coil and may be symmetrical to the center axis. This wave may be reflected by the reflector towards a focus area, which also may be a focus point. The focus area may be on the center axis and distant from the coil. The distance may be in a range between 2 cm and 25 cm depending on the design of the reflector and the coil to leave sufficient space for positioning a patient such that a concretion can be disintegrated or a soft tissue target area can be treated. The entirety of the waves propagating from the shockwave source to the focus area or focus point, define a wave propagation area.

The shockwave transducer may also includes an inner diffuser. Hence, the shockwave transducer may include an outer diffuser or an inner diffuser or both.

The shockwave source may include an inner diffuser. The inner diffuser may be coupled to the shockwave source, preferably the inner diffuser may be coupled to the rim of the shockwave source. The inner diffuser may have grooves and protrusions distributed around its circumference. The inner diffuser may include at least one segment. If the inner diffuser includes more than one segment, these segments may be coupled on the shockwave source. The inner diffuser may include only one piece. The inner diffuser may be annular, but any other form known to the person skilled in the art is also possible.

The cylindrical coil may be arranged with its center axis at the reflector center axis. The cylindrical coil may generate a cylindrical wave propagating in a radial direction of the coil and may be symmetrical to the center axis. This wave may be reflected by the reflector towards a focus area, which also may be a focus point. The focus area may be on the center axis and distant from the coil. The distance may be in a range between 2 cm and 25 cm depending on the design of the reflector and the coil to leave sufficient space for positioning a patient such that a concretion can be disintegrated or a soft tissue target area can be treated. The entirety of the waves propagating from the shockwave source to the focus area or focus point, define a wave propagation area.

The protrusions of the outer diffuser may protrude towards the center axis and the protrusions of the inner diffuser may protrude away from the center axis.

The protrusion of the outer diffuser or the protrusion of the inner diffuser may protrude into the area defined by the wave propagating out of the reflector. Alternatively, the protrusion of the inner diffuser and the outer diffuser may protrude into the area defined by the wave propagating out of the reflector.

BRIEF DESCRIPTION OF THE DRAWINGS

In the following, the invention will be described by way of examples, and without limitation of the general inventive concept, based on embodiments and with reference to the drawings.

Figure 1:
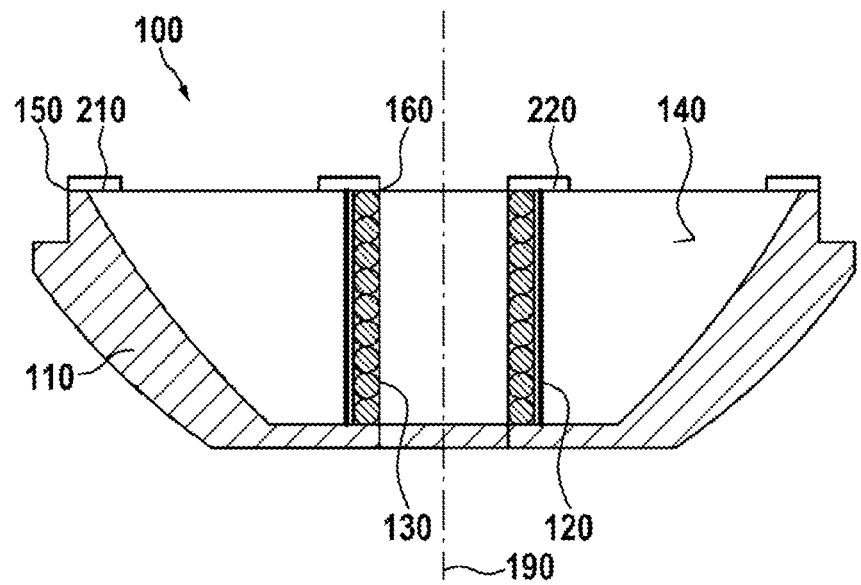
FIG. 1 is a sectional view of an exemplary embodiment of the shockwave transducer.

Generally, the drawings are not to scale. Like elements and components are referred to by like labels and numerals. For the simplicity of illustrations, not all elements and components depicted and labeled in one drawing are necessarily labels in another drawing even if these elements and components appear in such other drawing.

While various modifications and alternative forms, of implementation of the idea of the invention are within the scope of the invention, specific embodiments thereof are shown by way of example in the drawings and are described below in detail. It should be understood, however, that the drawings and related detailed description are not intended to limit the implementation of the idea of the invention to the particular form disclosed in this application, but on the contrary, the intention is to cover all modifications, equivalents and alternatives falling within the spirit and scope of the present invention as defined by the appended claims.

DETAILED DESCRIPTION

In FIG. 1 is a sectional view of an exemplary embodiment. The shockwave transducer 100 includes a reflector 110 and a shockwave source 130. The reflector 110 and the shockwave source 130 may be rotational symmetric and have a common center axis 190. The shockwave source may include a coil 120. The coil may have a cylindrical shape which may be defined by a cylindrical body on which the windings of the coil are held. Alternatively, the shockwave source the coil may include a flat coil or a piezo element or a spark gap, FIGS. 6a-6c. The reflector 110 may have a paraboloid shape such that a wave generated by the shockwave source 130 may be deflected on the inner surface 140 of the reflector 110 to a focus area 400 which may be on the common center axis 190. The shockwave transducer 100 has an outer diffuser 210. The outer diffuser 210 may be coupled to the rim 150 of the reflector 110. The shockwave transducer 100 may further include an inner diffuser 220. The inner diffuser 220 may be coupled to the shockwave source 130. The inner diffuser 220 may be coupled to the rim 160 of the shockwave source. The outer diffuser (210) may be rigidly coupled to the rim 150 of the reflector 110 and/or the inner diffuser (220) may be rigidly coupled to the shockwave source 130. In this exemplary embodiment the protrusions of the inner diffuser 222 and/or the outer diffuser 212 may be aligned approximately parallel (within ±10°, preferably ±5°, especially preferred ±2.5° or less) to a plane 182 passing through the rim 115.

Figure 2:
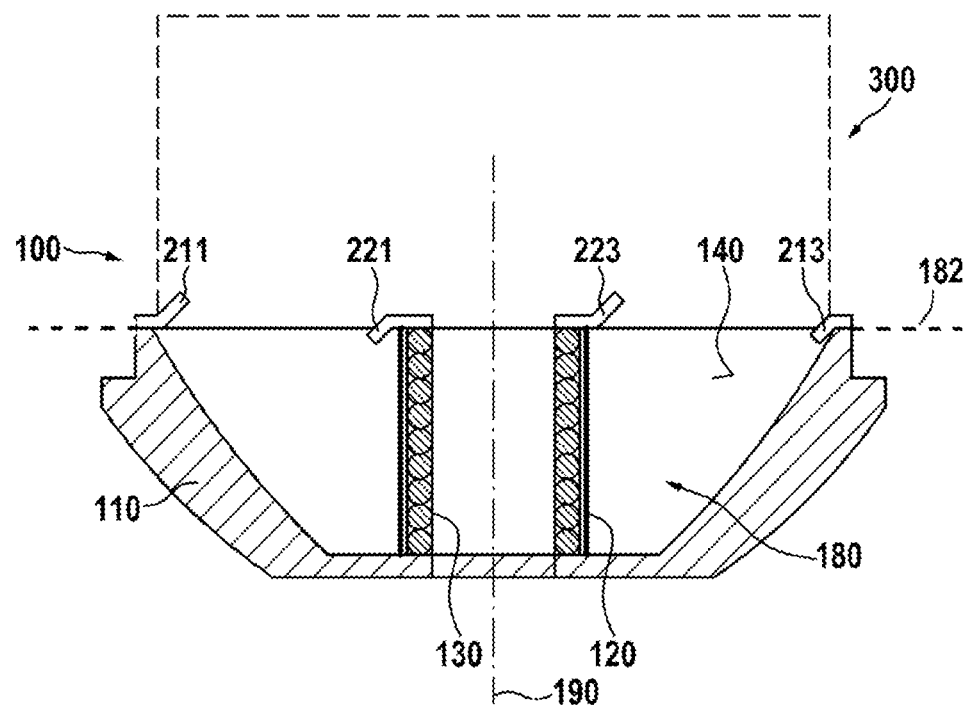
FIG. 2 is a sectional view of another an exemplary embodiment of the shockwave transducer.

As depicted exemplarily in FIG. 2, the protrusions of the inner diffuser 221 and/or the outer diffuser 213 may protrude inside the void of the reflector 180 or the protrusions of the inner diffuser 223 and/or the outer diffuser 211 may also protrude into a volume of a cylindrical space 300. The void of the reflector 180 may have a volume. The cylindrical space 300 may extend up to 0.5 cm, 1 cm, 2 cm, 5 cm or 10 cm from the rim of the reflector 150. The cylindrical space 300 may have a volume. The volume of the cylindrical space 300 may be the three-dimensional space enclosed by a physical, preferably an imaginary extension of the rim along the direction of the propagating wave and enclosing the wave propagation area.

Figure 3:
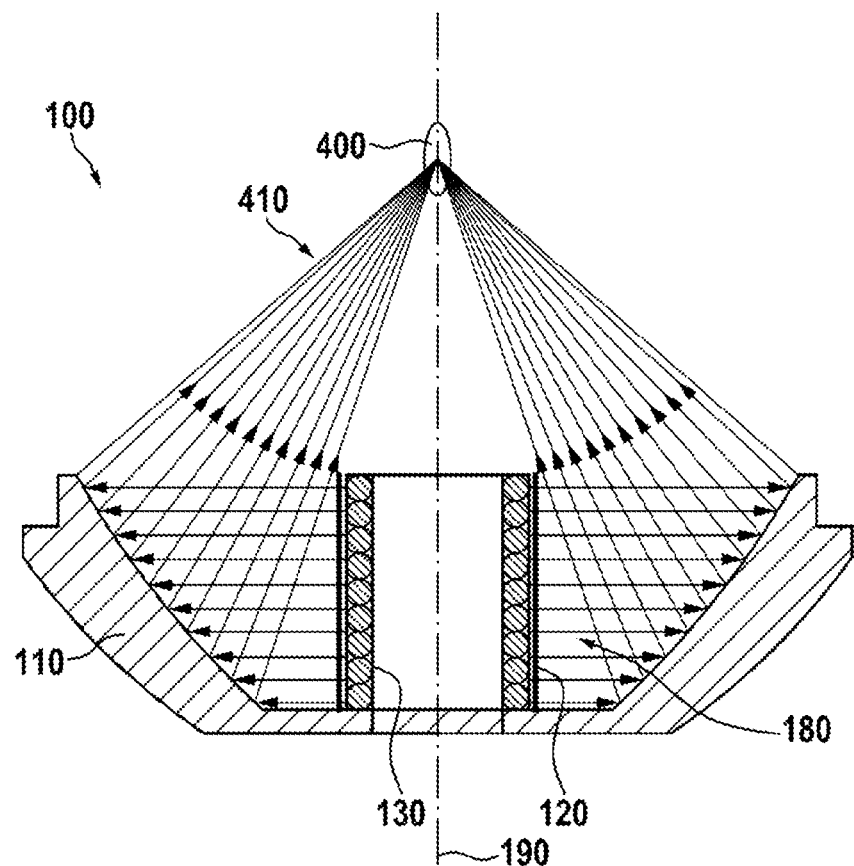
FIG. 3 illustrates the wave propagation.

FIG. 3 symbolizes the wave propagation 410 from the shockwave source 120 to a focus area 400. The reflector may be optimized such that a specific shape of the focus area 400 may be obtained. The entirety of the waves propagating 410 from the shockwave source 120 to the focus area or focus point 400, define the wave propagation area. The focus point 400 may be located on the center axis 190.

Figure 4:
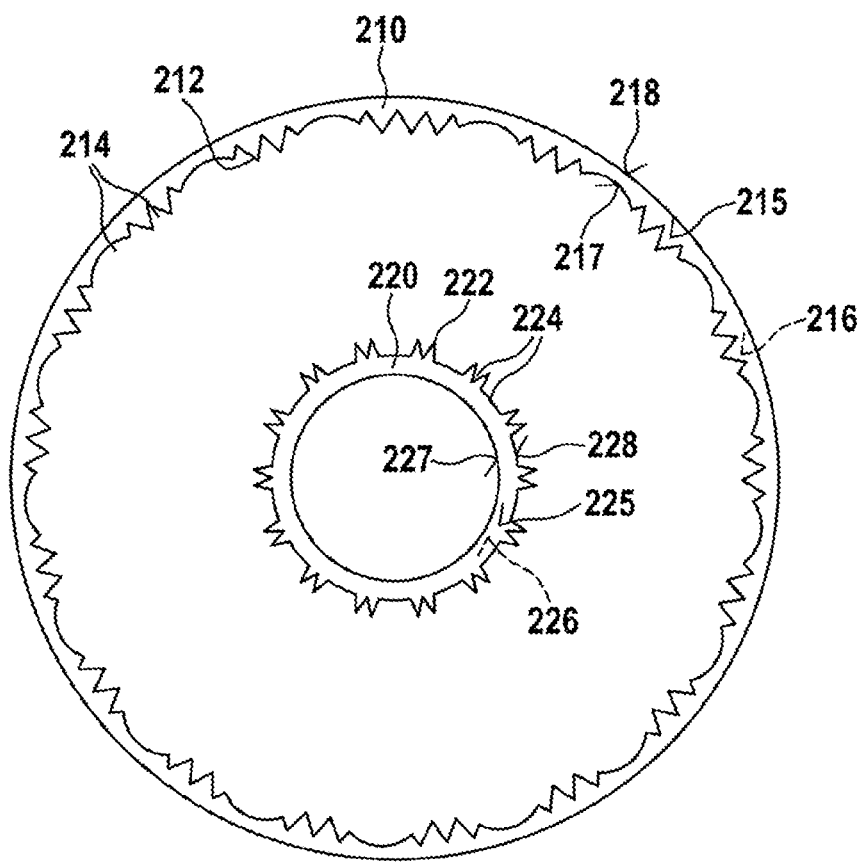
FIG. 4 is a top view of an outer diffuser and an inner diffuser.

FIG. 4 is an exemplary embodiment of the inner diffuser 220 and the outer diffuser 210. The inner diffuser 220 and the outer diffuser 210 may be annular. The outer diffuser 210 and the inner diffuser 220 may have a top side 215, 225, a bottom side 216, 226, a transducer-facing side 217, 227 and a transducer-averted side 218, 228. The outer diffuser and inner diffuser may also have grooves 214, 224 and protrusions 212, 222. The grooves 214, 224 and protrusions 212, 222 may be located on the transducer-facing side 217, 227 of the outer diffuser 210 and inner diffuser 220. The grooves 214, 224 and protrusions 212, 222 may be distributed around the circumference of the corresponding diffuser 210,220. The grooves 214, 224 and protrusions 212, 222 may be distributed regularly, preferably irregularly around the circumference of the outer 210 and/or inner diffuser 220.

Figure 5:
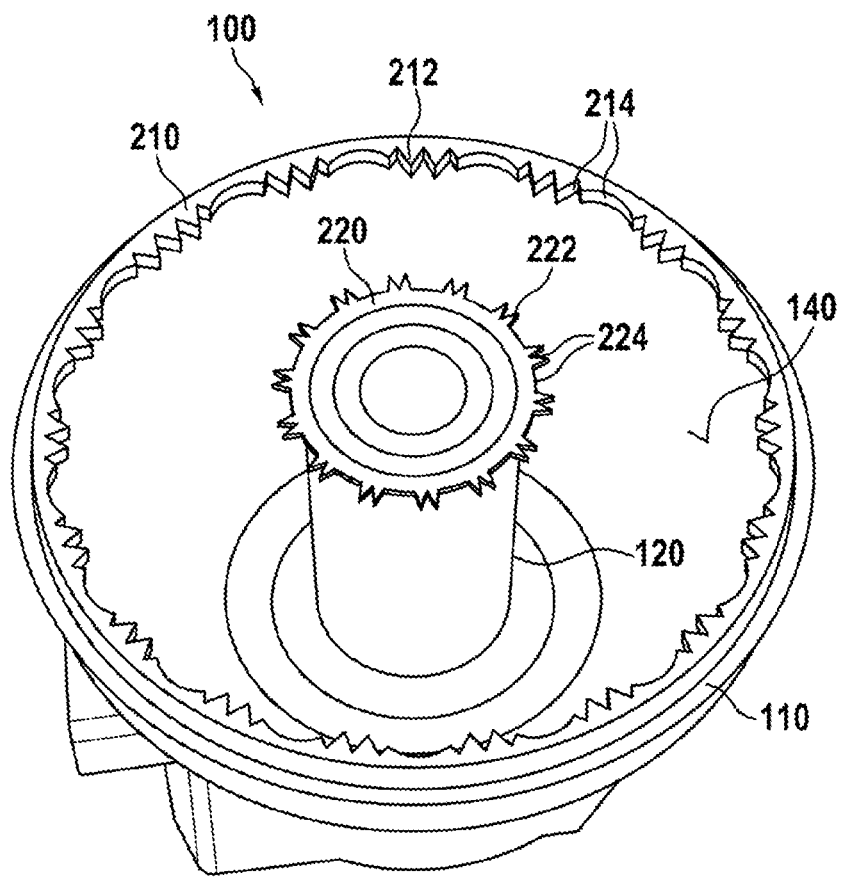
FIG. 5 is a perspective view of an exemplary embodiment of the shockwave transducer.
Figure 6A:
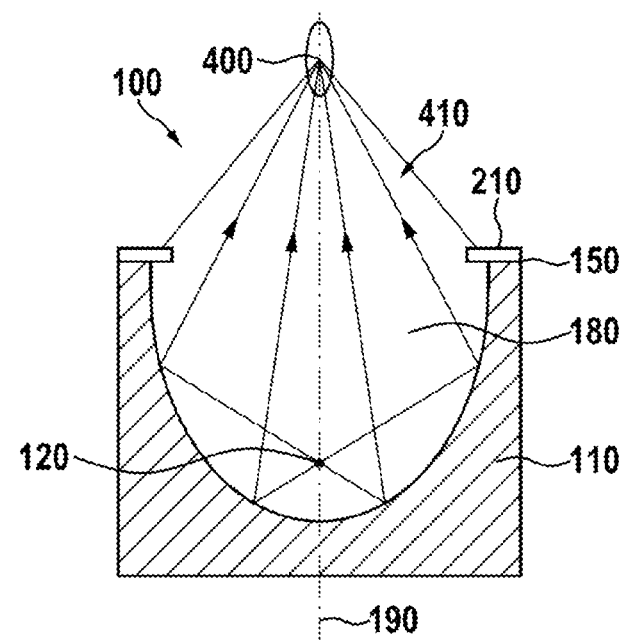
FIGS. 6a, 6b, and 6c are alternative exemplary embodiments of the shockwave transducer.

FIG. 5 is a perspective view of an exemplary embodiment of the shockwave transducer 100 according to FIG. 1. The outer diffuser 210 may be coupled to the rim 115 of the reflector 110. The inner diffuser 220 may be coupled to the rim 160 of the shockwave source 130. In this exemplary embodiment, the shockwave source 120 has a cylindrical shape and the reflector 110 may have a paraboloid shape. FIG. 6a is a sectional view of an exemplary embodiment.

FIG. 6a shows an electro-hydraulic ellipsoid. The shockwave source 120 may be located on the center axis of the body 110. The shockwave source may be a point source. The body 110 may include an ellipsoidal reflector. The reflector 110 may be rotational symmetric and have a center axis 190. The reflector 110 may have an ellipsoidal shape, such that a wave generated by the shockwave source 120 is deflected on the inner surface 140 of the reflector 110 to a focus area 400, which may be on the common center axis 190. The shockwave transducer 100 has a diffuser 210. The diffuser 210 may be coupled to the rim 150 of the reflector 110. The entirety of the waves propagating 410 from the shockwave source 120 to the focus area or focus point 400, define the wave propagation area. The at least one diffuser 210 may protrude inside the void of the reflector 180 and into the wave propagating area.

Figure 6B:
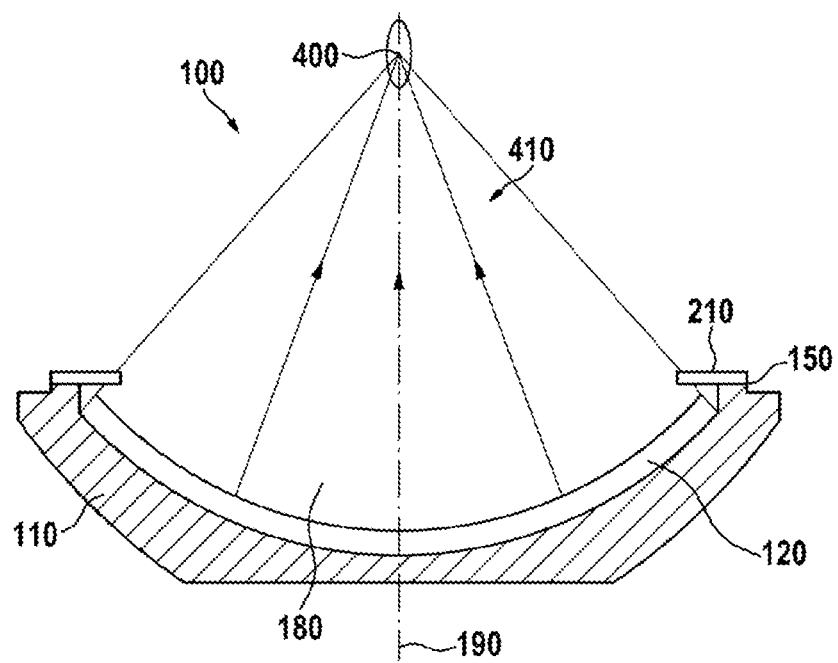

In FIG. 6b is a sectional view of another exemplary. FIG. 6b shows a shockwave transducer 100 with a piezo electric sphere. The body 110 may include a spherical section and the shock wave source 120 may be a spherical assembly of piezo elements. The shockwave source 120 may be self-focusing, e.g. does not need an additional focusing component. The body 110 may be rotational symmetric and have a center axis 190. The shockwave transducer 100 has at least one diffuser, which may be an outer diffuser 210. The diffuser 210 may be coupled to the rim 150 of the body 110. The entirety of the waves propagating 410 from the shockwave source 120 to the focus area or focus point 400, define the wave propagation area. The at least one diffuser 210 may protrude inside the void of the body 180 and into the wave propagating area.

Figure 6C:
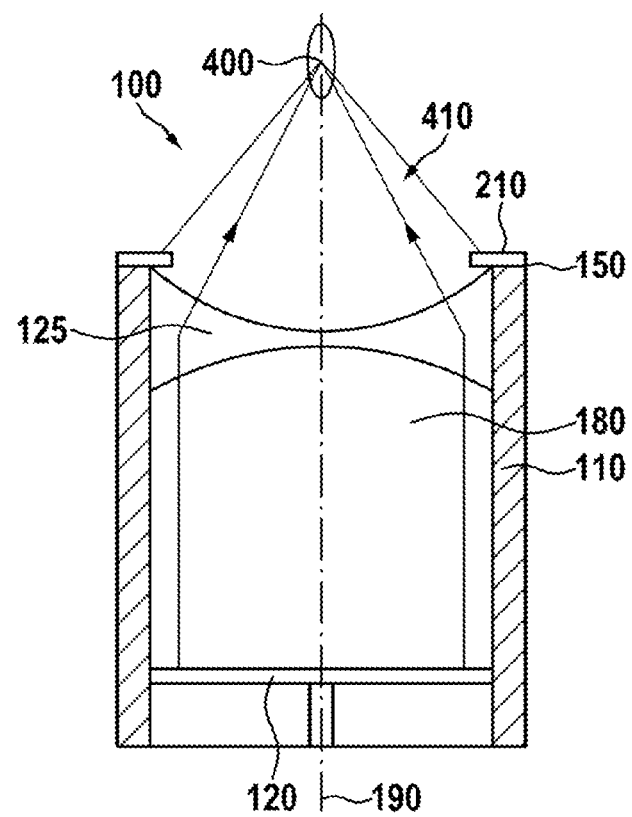

In FIG. 6c is a sectional view of another exemplary. FIG. 6c shows a shockwave transducer 100. The shockwave transducer may have a center axis 190. The shock wave source 120 may be a flat coil. The shockwaves generated by the flat coil may be focused, by a focus element 125. The focus element may be an acoustic lens. The acoustic lens may be part of the body 110. The shockwave transducer 100 has an outer diffuser 210. The outer diffuser 210 may be coupled to the rim 150 of the acoustic lens. The entirety of the waves propagating 410 from the shockwave source 120 to the focus area or focus point 400, define the wave propagation area. The at least one diffuser 210 may protrude inside the void of the body 180 and into the wave propagating area.

Figure 7:
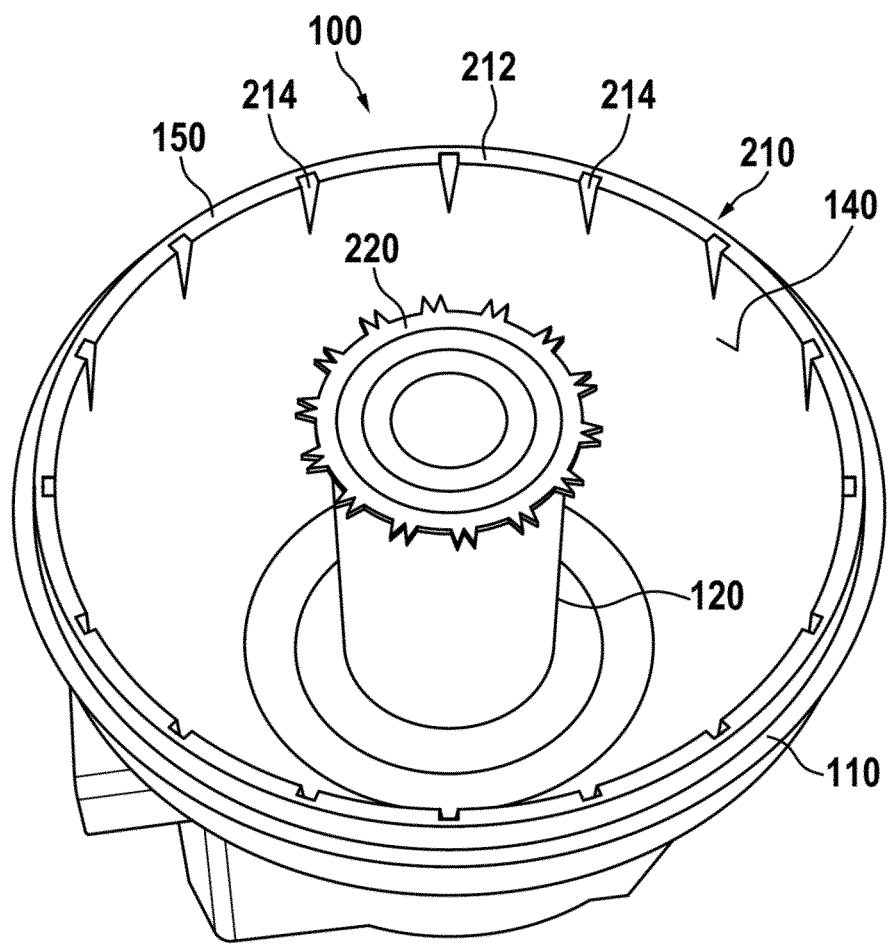
FIG. 7 is a perspective view of a further embodiment.

FIG. 7 is a perspective view of a further embodiment of the shockwave transducer 100. The at least one diffuser 210 may be part of the body 110 itself. For example, the body 110 may include the outer diffuser 210 and/or the inner diffuser 220 may be arranged on the shockwave source 120. The body 110 may be a reflector. The grooves 214 of the outer diffuser 210 may be formed by recesses and/or notches within the body 110. The grooves 214 may penetrate the rim 150 and/or the inner surface 140 of the body, but may not penetrate through the outer surface of the body 110. The protrusions 212 of the outer diffuser 210 may be part of the body 110 without the grooves 214. In other words, the protrusions 212 may be part of the body 110 without recesses in the rim 150 and/or the inner surface 140. Such, the diffuser include a shockwave reflecting material from the body. The grooves 214 may be inserted into the body 110 e.g. by cutting, milling, drilling and/or sawing. The grooves 214 inserted into the body 110 may for example be rectangular, triangular and/or parabolic. The grooves 214 and protrusions 212 of the outer diffuser may be distributed around the circumference of the body 110 and/or the rim 150. The grooves 214 and protrusions 212 may be distributed regularly, preferably irregularly around the circumference of the body 110 and/or the rim 150. The grooves 214 and protrusions 212 of the outer diffuser may be rigidly arranged on the circumference of the body 110 and/or the rim 150.

Figure 8:
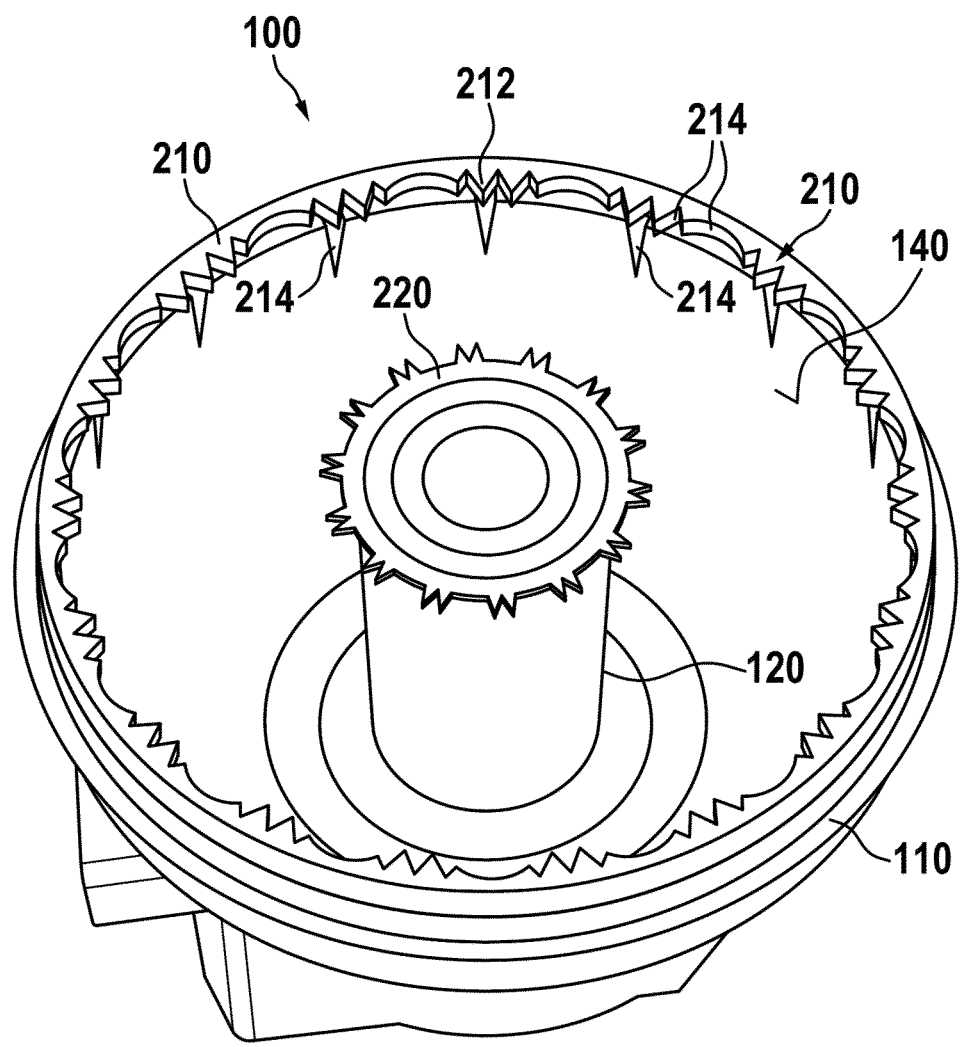
FIG. 8 is a combination of the embodiments of FIG. 5 and FIG. 7.

FIG. 8 is a perspective view of another embodiment of the shockwave transducer 100. This embodiment is a combination of the embodiment of FIG. 5 and FIG. 7. In this embodiment, the outer diffuser may be the body itself in combination with a complementary diffuser (outer diffuser) of the embodiment according to FIG. 5. The transducer facing side of the complementary diffuser may face the grooves formed in the body.

It will be appreciated to those skilled in the art having the benefit of this disclosure that implementations of this invention are directed to provide shockwave transducers in medical shockwave devices such as lithotripters which generate shockwaves in a medium, e.g. water, and couple them into a human or animal body. Further modifications and alternative embodiments of various aspects of the invention will be apparent to those skilled in the art in view of this description. Accordingly, this description is to be construed as illustrative only and is provided for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 shockwave transducer
110 body
120 shockwave source
125 focus element
130 coil
140 inner surface
150 rim exit aperture
160 rim of the shockwave source
180 void body
182 plane
190 center axis
210 outer diffuser
211-213 protrusion
214 groove
215 top side
216 bottom side
217 transducer-facing side
218 transducer-averted side
220 inner diffuser
221-223 protrusion
224 groove
225 top side
226 bottom side 227 transducer-facing side
228 transducer-averted side
300 cylindrical space
400 focus area
410 wave propagation

The invention claimed is:

1. A shockwave transducer for a medical shockwave device, the transducer comprising:
a body that has a void filled with a shockwave-conducting medium, the body holding a shockwave source configured to generate shockwaves, the body further comprising an exit aperture dimensioned for the shockwaves to exit the body,
wherein the transducer is configured to direct the shockwaves propagating through the exit aperture,
wherein the body comprises at least one diffuser that is rigidly arranged at the exit aperture, the at least one diffuser comprising a material with a propagation velocity of the shockwave that is different from a propagation velocity of the shockwave in the shockwave-conducting medium.

2. A shockwave transducer according to claim 1,
wherein the at least one diffuser extends into the void of the body and/or extends into a cylindrical space that has the same base as the exit aperture and extends from the body.

3. A shockwave transducer according to claim 2,
wherein the cylindrical space has a height between 0.5 cm and 30 cm.

4. A shockwave transducer according to claim 1,
wherein the at least one diffuser is engaging into the shockwave upon propagation thereof from the shockwave source.

5. A shockwave transducer according to claim 1,
wherein the at least one diffuser is an outer diffuser arranged annularly at an outer circumference of the exit aperture and/or the at least one diffuser is an inner diffuser arranged annularly at an inner circumference of the exit aperture.

6. A shockwave transducer according to claim 1,
wherein the at least one diffuser has grooves and protrusions distributed around a circumference of the at least one diffuser.

7. A shockwave transducer according to claim 6,
wherein the grooves and protrusions are distributed irregularly around the circumference of the at least one diffuser.

8. A shockwave transducer according to claim 1,
wherein the body has a center axis and protrusions distributed around a circumference of the at least one diffuser, wherein the protrusions protrude radially with respect to the center axis.

9. A shockwave transducer according to claim 1,
wherein the at least one diffuser comprises a polymeric material.

10. A shockwave transducer according to claim 1,
wherein the at least one diffuser comprises a material configured to reflect a shockwave.

11. A shockwave transducer according to claim 1,
wherein the at least one diffuser comprises a material in which a propagation speed of the shockwave differs from a propagation speed of the shockwave in water.

12. A shockwave transducer according to claim 1,
wherein the shockwave transducer comprises a flat coil or a spherical assembly of piezo elements or a spark gap.

13. A shockwave transducer according to claim 1,
wherein the at least one diffuser comprises a metal.

14. A shockwave transducer according to claim 1,
wherein the body comprises a reflector having a center axis and the at least one diffuser is located at a rim of the reflector, and the shockwave transducer comprises a cylindrical coil having a coil center axis, the coil center axis being arranged at the reflector center axis of the reflector.

15. A medical shockwave device comprising a shockwave transducer according to claim 1.

* * * * *